United States Patent
Berlin (10) Patent No.: US 7,118,868 B2
(45) Date of Patent: Oct. 10, 2006

(54) METHOD FOR DETECTING CYTOSINE METHYLATIONS

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 398 days.

(21) Appl. No.: 10/311,661

(22) PCT Filed: Jun. 19, 2001

(86) PCT No.: PCT/DE01/02274

§ 371 (c)(1),
(2), (4) Date: Dec. 18, 2002

(87) PCT Pub. No.: WO01/98528

PCT Pub. Date: Dec. 27, 2001

(65) Prior Publication Data

US 2004/0152080 A1    Aug. 5, 2004

(30) Foreign Application Priority Data

Jun. 19, 2000   (DE)   ............................. 100 29 915

(51) Int. Cl.
    *C12Q 1/68*   (2006.01)
(52) U.S. Cl. .................... 435/6; 435/91.1; 435/91.2
(58) Field of Classification Search ............... None
    See application file for complete search history.

(56) References Cited

FOREIGN PATENT DOCUMENTS

WO    WO 00/31294    6/2000

OTHER PUBLICATIONS

Oxis Research (http://www.oxisresearch.com/products/chemicals/peroxynitrite/33113/33113.shtml (Jul. 19, 2005).*
Herman et al, Proc. Natl. Acad. Sci. USA 93: 9821 (1996).*
USB Molecular Biology Reagents/Protocols 1992, United States Biochemical Corporation, 1992, Cleveland, OH, pp. 218-219.*
Xiong et al., 'COBRA: a sensitive and quantitative DNA methylation assay.' Nucleic Acids Research, 25(12):2532-4 (1997).

* cited by examiner

*Primary Examiner*—James Martinell
(74) *Attorney, Agent, or Firm*—Kriegsman & Kriegsman

(57) ABSTRACT

A method is described for the detection of 5-methylcytosine in genomic DNA samples. First, a genomic DNA from a DNA sample is chemically converted with a reagent, whereby 5-methylcytosine and cytosine react differently. Then the pretreated DNA is amplified with the use of a polymerase with primers of different sequence. In the next step, the amplified genomic DNA is hybridized to an oligonucleotide array and PCR products are obtained, which must be provided with a label. Alternatively, the PCR products can be extended in a primer extension reaction, wherein the extension products are also provided with a label.

In the last step, the extended oligonucleotides are investigated for the presence of the label.

24 Claims, 1 Drawing Sheet

Fig. 1

METHOD FOR DETECTING CYTOSINE METHYLATIONS

BACKGROUND OF THE INVENTION

The present invention concerns a method for the detection of cytosine methylabons in DNA.

The levels of observation that have been well studied due to method developments in recent years in molecular biology include the genes themselves, as well as [transcription and] translation of these genes into RNA and the proteins arising therefrom. During the course of development of an individual, when a gene is turned on and how the activation and inhibition of certain genes in certain cells and tissues are controlled can be correlated with the extent and nature of the methylation of the genes or of the genome. Pathogenic states are also expressed by a modified methylation pattern of individual genes or of the genome.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest 5-Methylcytosine positions, however, cannot be identified by sequencing, since 5-methylcytosine has the same base-pairing behavior as cytosine. In addition, in the case of a PCR amplification, the epigenetic information, which is borne by 5-methylcytosines, is completely lost.

A relatively new method that has since been applied most frequently for investigating DNA for 5-methylcytosine is based on the specific reaction of bisulfate with cytosine, which is converted to uracil, which corresponds in its base-pairing behavior to thymidine, after a subsequent alkaline hydrolysis. In contrast, 5-methylcytosine is not modified under these conditions. Thus the original DNA is converted, such that methylcytosine, which originally cannot-be distinguished from cytosine by means of its hybridizabon behavior, now can be detected by "standard" molecular biological techniques as the single remaining cytosine, for example, by amplification and hybridizaton or sequencing. All of these techniques are based on base pairing, which now is fully utilized. The prior art, which concerns sensitivity, is defined by a method that incorporates the DNA to be investigated in an agarose matrix, through which diffusion and renaturation of the DNA is prevented (bisulfate reacts only on single-stranded DNA) and all precipitation and purification steps are replaced by rapid dialysis (Olek A., et al., Nucl. Acids Res. 1996, 24, 5064–5066). Individual cells can be investigated with this method, which illustrates the potential of the method. Of course, previously, only individual regions of up to approximately 3000 base pairs in length have been investigated; a global investigation of cells for thousands of possible methylation analyses is not possible. Of course, this method also cannot reliably analyze very small fragments comprised of small sample quantities. These are lost despite the protection from diffusion through the matrix.

A review of the other known possibilities for detecting 5-methylcytosines can be derived from the following review article: Rein T., DePamphilis, M. L., Zorbas H., Nucleic Acids Res. 1998, 26, 2255.

The bisulfate technique has previously been applied only in research, with a few exceptions (e.g., Ze[s]chnigk M. et al., Eur. J Hum. Gen. 1997, 5, 94–8). However, short, specific pieces of a known gene are always amplified after a bisulfate treatment and either completely sequenced (Olek A. and Walter, J., Nat Genet. 1997, 17, 275–276) or individual cytosine positions (Gonzalgo M. L. and Jones P. A., Nucl. Acids Res. 1997, 25, 2529–2531, WO Patent 95 00669) or an enzyme cleavage (Xiong Z. and Laird P. W., Nucl. Acids Res. 1997, 25, 2532–2534) are detected by a "primer extension reacton". Also, detection by means of hybridizing has been described (Olek et al., WO 99/28498).

Other publications, which are concerned with the application of the bisulfate technique for the detection of methylation in individual genes are: Xiong, Z. and Laird, P. W. (1997), Nucl. Acids Res. 25, 2532; Gonzalgo, M. L. and Jones, P. A. (1997) Nucl. Acids Res. 25, 2529; Grigg S. and Clark S. (1994) Bioassays16, 431; Zeschnigk, M. et al, (1997) Human Molecular Genetics 6, 387; Teil R. et al. (1994), Nucl. Acids Res. 22, 695; Martin V. et al. (1995), Gene. 157, 261; WO 97/46705, WO 95/15373 and WO 45560.

A review of the prior art in oligomer array production can be taken from a special publication of Nature Genetics that appeared in January 1999 (Nature Genetics Supplement, Volume 21, January 1999), the literature cited therein and, U.S. Pat. No. 5,994,065 on methods for the production of solid carriers for target molecules such as oligonucleotides with reduced nonspecific background signal.

Probes with many fluorescent labels have been used for the scanning of an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, in addition to many others, are commercially available.

Matrix-assisted laser desorption/ionization mass spectrometry (MALDI-TOF) is a very powerful development for the analysis of biomolecules (Karas M., and Hillenkamp F. (1988) Laser desorption ionization of proteins with molecular masses exceeding 10,000 daltons. (1998) Anal. Chem. 60, 2299–2301). An analyte is embedded in a light-absorbing matrix. The matrix is evaporated by means of a short laser pulse and the analyte molecule is transported unfragmented into the gas phase. The ionization of the analyte is achieved by collisions with matrix molecules. An applied voltage accelerates the ions in a field-free flight tube. The ions are accelerated to a varying extent based on their different masses. Smaller ions reach the detector sooner than larger ions.

MALDI-TOF spectroscopy is excellently suitable for the analysis of peptides and proteins. The analysis of nucleic acids is somewhat more difficult (Gut, I. G. and Beck, S. (1995)), DNA and Matrix Assisted Laser Desorption Ionization Mass Spectrometry. Molecular Biology: Current Innovations and Future Trends 1: 147–157.) For nucleic acids, the sensitivity is approximately 100 times poorer than for peptides and decreases overproportionally with increasing fragment size. For nucleic acids, which have a backbone with multiple negative charges, the ionization process through the matrix is essentially less efficient. In MALDI-TOF spectroscopy, the selection of the matrix plays a very important role. For the desorption of peptides, several very powerful matrices have been found, which produce a very fine crystallization. Several high-performing matrices have been found in the meantime for DNA, but the difference in sensitivity has not been reduced in this way. The difference in sensitivity can be reduced by modifying the DNA chemically in such a way that it is similar to a peptide.

Phosphorothioate nucleic acids, in which the usual phosphates of the backbone are substituted by thiophosphates, can be converted into a charge-neutral DNA by simple alkylation chemistry (Gut, I. G. and Beck, S. (1995), A procedure for selective DNA alkylation and detection by mass spectrometry. Nucleic Acids Res. 23: 1367–1373). The coupling of a "charge tag" to this modified DNA results in an increase in sensitivity by the same amount that is found for peptides. Another advantage of "charge tagging" is the increased stability of the analysis against impurities, which greatly interfere with the detection of unmodified substrates.

Genomic DNA is obtained by standard methods from DNA of cells,.tissue or other test samples. This standard methodology is found in references such as Fritsch and Maniatis, eds., Molecular Cloning: A Laboratory Manual, 1989.

Urea improves the efficiency of the bisulfate treatment prior to sequencing of 5-methylcytosine in genomic DNA (Paulin, R. Grigg GW, Davey MW, Piper AA. (1998), Nucleic Acids Res. 26: 5009–5010).

SUMMARY OF THE INVENTION

The object of the present invention is thus to make available a method for the detection of cytosine methylations in DNA, which overcomes the disadvantages of the prior art.

The object is solved in that a method for the detection of cytosine methylations in DNA is made available, wherein the following operating steps are conducted:

a) a genomic DNA sample is incubated with a solution of a bisulfite (=hydrogen sulfite, disulfite) in the concentration range between 0.1 and 6 mol/liter, whereby a denaturing reagent and/or solvent as well as at least one radical trap is present;

b) the treated DNA sample is diluted with water or an aqueous solution;

c) the DNA sample is amplified in a polymerase reaction;

d) one detects how much the sequence has changed by the treatment according to step a) in comparison to the genomic DNA sample and concludes the methylation state of at least one locus in the genomic DNA sample.

It is preferred according to the invention that the denaturing reagent and/or solvent is selected from the following list of compounds or compound classes:

Polyethylene glycol dialkyl ethers, dioxane and substituted derivatives, urea or derivatives, acetonitrile, primary alcohols, secondary alcohols, tertiary alcohols, diethylene glycol dialkyl ethers, triethylene glycol dialkyl ethers, tetraethylene glycol dialkyl ethers, pentaethylene glycol dialkyl ethers, hexaethylene glycol dialkyl ethers, DMSO, THF.

It is additionally preferred that the radical trap is selected from the following group of compounds: di- and trihyroxybenzenes, green tea extract, pine bark extract, gingko biloba extract, (EGb 761), flavonoid mixture of different fruit and vegetable extracts (GMLD), Bio-Normalizer (Sun-O Corp),. DPPH (1,1-diphenyl-2-picrylhydrazyl), NDGA (nordihydroguaiaretic acid), Trolox (6-hydroxy-2,5-7,8-tetramethylchromane 2-carboxylic acid), 2,6-di-tert-butylphenol, 4-methyl-di-tert-butylphenol, 4-methoxy-di-tert-butylphenol, 2,6-di-tert-butyl-p-cresol, 3,4-dihydroxybenzoic acid, vitamin C, vitamin E, vitamin Q, hydroquinone, ubiquinone, lignans, hydroxyterpenes, flavonoids, curcumin, tannins, retinoic acid compounds, Ge-132 bis-beta-carboxyethylgermanium sesquioxide, superoxide dismutase (SOD), superoxide catylase, alpha-naphthoflavone, di(2-methyl-5-chlorophenyl)dithionate and Cu(II) derivatives, mebendazole, CS (chloroform-soluble) alkyloid extract, 4-(3,5-di-tert-butyl-4-hydroxyphenyl)3-hydroxy-1,2-naphthoquinone, 4-(3,5-di-tert-butyl-4-hydroxyphenyl)3-methoxy-1,2-naphthoquinone, 4-(3,5-di-tert-butyl-4-hydroxyphenyl)1,2-naphthoquinone, 2-(3,5-di-tert-butyl-4-hydroxyphenyl)3-bromo-1,4-naphthoquinone, 2-(3,5-di-tert-butyl-4-hydroxyphenyl)3-chloro-1,4-naphthoquinone, 2-(3,5-di-tert-butyl-4-hydroxyphenyl)3-methoxy-1,4-naphthoquinone, 2-(3,5-di-tert-butyl-4-hydroxyphenyl)3-hydroxy-1,4-naphthoquinone, 2-(3,5-di-tert-butyl-4-hydroxyphenyl)1,4-naphthoquinone, 4-(3,5-di-tert-butyl-4-hydroxyphenyl)3-hydroxy-5,5,8,8-tetramethyl-5,6,7,8-tetrahydro-1,2-anthraquinone, 4-(3,5-di-tert-butyl-4-hydroxyphenyl)3-methoxy-5,5,8,8-tetramethyl-5,6,7,8-tetrahydro-1,2-anthraquinone, 4-(3,5-di-tert-butyl-4-hydroxyphenyl)-5,5,8,8-tetramethyl-5,6,7,8-tetrahydro-1,2-anthraquinone, 3-bromo-4-(3,5-di-tert-butyl-4-hydroxyphenyl)-5,5,8,8-tetramethyl-5,6,7,8-tetrahydro-1,2-anthraquinone, 2-(3,5-di-tert-butyl-4-oxocyclohexa-2,5-dienylidine)indan-1,3-dione, 2-(3,5-di-tert-butyl-4-oxocyclohexa-2,5-dienylidine)3,4-epoxy-3-hydroxy-4-methoxy-(3,4-dihydro-2H-naphthalen-1-one, 2-(3,5-di-tert-butyl-4-oxocyclohexa-2,5-dienylidine)3,4-epoxy-3,4-dimethoxy-(3,4-dihydro-2H-naphthalen-1-one, 3,3-bi-[2-(3,5-di-tert-butyl-4-hydroxyphenyl)indan-1-on]-3-yl, 2-(3,5-di-tert-butyl-4-hydroxyphenyl)3-bromo-5,5,8,8-tetramethyl-5,6,7,8-tetrahydro-1,4-anthraquinone, 2-(3,5-di-tert-butyl-4-hydroxyphenyl)3-chloro-5,5,8,8-tetramethyl-5,6,7,8-tetrahydro-1,4-anthraquinone, 2-(3,5-di-tert-butyl-4-hydroxyphenyl)3-methoxy-5,5,8,8tetramethyl-5,6,7,8-tetrahydro-1,4-anthraquinone, 2-(3,5-di-tert-butyl-4-hydroxyphenyl)3-hydroxy-5,5,8,8-tetramethyl-5,6,7,8-tetrahydro-1,4-anthraquinone, 2-(3,5-di-tert-butyl-4-hydroxyphenyl)-5,5,8,8-tetramethyl-5,6,7,8-tetrahydro-1,4-anthraquinone, 2-bromo-3-(3-bromo-5-tert-butyl-4-hydroxyphenyl)-5,5,8,8-tetramethyl-5,6,7,8-tetrahydro-1,4-anthraquinone, 2-bromo-33,5-dibromo-4-hydroxyphenyl)-5,5,8,8-tetramethyl-5,6,7,8-tetrahydro-1,4-anthraquinone, 2-bromo-3-(3-bromo-5-tert-butyl-4-hydroxyphenyl)3-hydroxy-5,5,8,8-tetramethyl-5,6,7,8-tetrahydro-1,4-anthraquinone, 3-bromo-2-(3,5-di-tert-butyl-4-hydroxyphenyl)1,4-anthroquinone, 2-(3,5-di-tert-butyl-4-hydroxyphenyl)3-methoxy-1,4-anthraquinone, 2-(3,5-di-tert-butyl-4-hydroxyphenyl)3-hydroxy-1,4-anthraquinone, 5,5,8,8-tetramethyl-5,6,7,8-tetrahydronapthalene-1,3-diol, 3-methoxy-5,5,8,8-tetramethyl-5,6,7,8-tetrahydronaphthalen-1-ol, 4-(3-chloro-5,5,8,8-tetramethyl-1,4-dioxo-1,4,5,6,7,8-hexahydroanthracen-2-yl)benzoic acid, methyl-4-(3-chloro-5,5,8,8-tetramethyl-1,4-dioxo-1,4,5,6,7,8-hexahydroanthracen-2-yl)benzoate, 4-(3-hydroxy-1,4-dioxo-1,4-dihydronaphthalen-2-yl)benzoic acid, methyl-(3-methoxy-1,4-dioxo-1,4dihydronaphthalen-2-yl)benzoic acid, 4-(3-hydroxy-5,5,8,8-tetramethyl-1,4-dioxo-1,4,5,6,7,8-hexahydroanthracen-2-yl)benzoic acid, methyl-4-(3-hydroxy-1,4-dioxo-1,4-dihydronaphthalen-2-yl-azo)benzoate, 4-(3-hydroxy-5,5,8,8-tetramethyl-1,4-dioxo-1,4,5,6,7,8-hexahydroanthracen-2-yl-azo)benzoic acid, 3-(3,5-di-tert-butylxocyclohexa-2,5-dienylidine)5,5,8,8-tetramethyl-5,6,7,8-tetrahydrocycdopenta[b]naphthalen-1,2-dione, 3-(3,5-di-tert-butyl-4-oxocyclohexa-2,5-dienylidene)5,5,8,8-tetramethyl-5,6,7,8-tetrahydroanthracen-3H-1,2,4-trione, 2-(3,5-di-tert-butyl-4-hydroxyphenyl)3-methoxy-5,8-dimethyl-1,4-naphthoquinone, 2-(3,5-di-tert-butyl-4-hydroxyphenyl)3-methoxy-6,7-dimethyl-1,4-naphthoquinone, 2-(3,5-di-tert-butyl-4-hydroxyphenyl)3-methoxy-5-methyl-1,4-naphthoquinone, 2-(3,5-di-tert-butyl-4-hydroxyphenyl) 2-methoxy-5-methyl-1,4-naphthoquinone, 2-(3,5-di-tert-butyl-4-hydroxyphenyl)3-methoxy-6-methyl-1,4-naphthoquinone, 3-(3,5-di-tert-butyl-4-hydroxyphenyl)2-methoxy-6-methyl-1,4-naphthoquiniione, 2-(3,5-di-tert-butyl-4-hydroxyphenyl)3-methoxy-5,6-dimethyl-1,4-naphthoquiniione, 3-(3,5-di-tert-butyl-4-hydroxyphenyl)2-methoxy-5,6-dimethyl-1,4-naphthoquinone, 2-(3,5-di-tert-butyl-4-hydroxyphenyl)-3-methoxy-5,7-dimethyl-1,4-naphthoquinone, 3-(3,5-di-tert-butyl-4-hydroxyphenyl)2-methoxy-5,7-dimethyl-1,4-naphthoquinone, 2-(3,5-di-tert-butyl-4-hydroxyphenyl)3-ethylthio-5-methyl-1,4-naphthoquinone, 2-(3,5-di-tert-butyl-4-hydroxyphenyl)3-ethylthio-6-methyl-1,4-naphthoquinone, 2-(3,5-di-tert-butyl-4-hydroxyphenyl)3-hydroxy-5,8-dimethyl-1,4-naphthoquinone, 2-(3,5-di-tert-butyl-4-hydroxyphenyl)3-hydroxy-6,7-dimethyl-1,4-naphthoquinone, 2-(3,5-di-tert-butyl-4-hydroxyphenyl)3-hydroxy-5-methyl-1,4-naphthoquinone, 3-(3,5-di-tert-butyl-4-hydroxyphenyl)2-hydroxy-5-methyl-1,4-naphthoquinone, 2-(3,5-di-tert-butyl-4-hydroxyphenyl)3-hydroxy-6-methyl-1,4-naphthoquinone, 3-(3,5-di-tert-butyl-4-hydroxyphenyl)2-hydroxy-6-methyl-1,4-naphthoquinone, 2-(3,5-di-tert-butyl-4-hydroxyphenyl)3-hydroxy-5,6-dimethyl-1,4-naphthoquinone, 2-(3-bromo-5-tert-butyl-4-hydroxyphenyl)3-hydroxy-5,6-dimethyl-1,4-naphthoquinone, 3-(3,5-di-tert-butyl-4-hydroxyphenyl)-2-hydroxy-5,6-dimethyl-1,4-naphthoquinone, 2-(3,5-di-tert-butyl-4-hydroxyphenyl)3-hydroxy-5,7-dimethyl-1,4-naphthoquinone, 3-(3,5-di-tert-butyl-4-hydroxyphenyl)2-hydroxy-5,7-dimethyl-1,4-naphthoquinone.

According to the invention, it is preferred that the genomic DNA sample is thermally denatured prior to the treatment.

According to the invention, it is particularly preferred that step c) is conducted in two substeps as follows:

a) a PCR preamplification with at least one pair of primers of different sequence, which hybridize nonspecifically to a DNA sample pretreated according to claim 1 and thus resulting in more than one amplified product in the PCR step;

b) a PCR amplification of the product formed in the preamplification with primers of different sequence, which are identical each time with a segment of the DNA sample [(+)-strand or (−)-strand] pretreated according to claim 1 or, vice-versa, are complementary [to it], and which specifically hybridize to the DNA to be amplified.

It is also preferred according to the invention that the amplification of several DNA segments is conducted in one reaction vessel.

It is also preferred according to the invention that a heat-stable DNA polymerase is used for the polymerase reaction.

It is particularly preferred according to invention that a desulfonation of the DNA is conducted prior to step c) of the method of the invention.

It is also preferred that the PCR products are hybridized to an oligonudeotide array for the detection of the pretreated DNA and then the following sub-steps are conducted:

a) the amplified genomic DNA is hybridized to at least one oligonucleotide with the formation of a duplex, wherein said hybridized oligonudeotides are directly adjacent by their 3' end or at a distance of up to 10 bases to the positions that are to be investigated relative to their methylation in the genomic DNA sample;

b) the oligonucleotide with known sequence of n nucleotides is extended by at least one nucleotide by means of a polymerase, whereby the nucleotide bears a detectable label and the extension depends on the methylation state of the respective cytosine in the genomic DNA sample.

It is preferred according to the invention that the PCR products are hybridized to an oligonucleotide array for the detection of the pretreated DNA and then the following sub-steps are conducted:

a) a set of oligonucleoudes is hybridized to the amplified genomic DNA with the formation of a duplex, whereby this set of oligonucleotides is comprised of two different species, and whereby the hybridized oligonudeotides of the first species are directly adjacent by their 3' end or at a distance of up to 10 bases to the positions that are to be investigated relative to their methylation in the genomic DNA sample, and whereby the second oligonucleotide of the second species hybridizes to a second region of the target molecule, so that the 5' end of the oligonucleotide of the second species is separated by a gap of the size of a single nucleotide or up to 10 nucleotides from the 3' end of the hybridized oligonucleotide of the first species at the site of said selected position;

(b) the oligonucleotide of the first species with known sequence of n nucleotides is extended by means of a polymerase by at most the number of nucleotides that lie between the 3' end of the oligonucleotide of the first species and the 5' end of the oligonudeotide of the second species, whereby the extension depends on the methylation state of the respective cytosine in the genomic DNA sample;

(c) the oligonucleotides are incubated in the presence of a ligase, whereby the adjacent oligonudeotide of the first species, which is extended by the polymerase reaction, and the oligonudeotide of the second species are connected and in this way a ligation product is obtained, as long as, in the preceding step, an extension of the oligonucleotide of the first species has resulted such that the 3' end with the present 3'-hydroxy function of the extended oligonucleotide is now directly adjacent to the 5' end of the oligonucleotide of the second species.

It is particularly preferred according to the invention that the oligonucleotides of the first species that are used and/or the oligonucleotides of the second species that are used either contain only the bases T, A and C or the bases T, A and G.

It is also preferred according to the invention that the PCR products are hybridized to an oligonucleotide array for the detection of the pretreated DNA and then the following sub-steps are conducted:

(a) the amplified genomic DNA is hybridized to at least one oligonucleotide with known sequence of n nucleotides with the formation of a duplex, wherein said hybridized oligonucleotides hybridize by their 3' end partially or completely to the positions which are to be investigated with respect to their methylation in the generic DNA sample;

(b) the oligonucleotide is extended by at least one nucleotide by means of a polymerase, as long as it has hybridized to the position to be investigated by its 3' terminus beforehand without erroneous base pairing, whereby at least one nucleotide bears a detectable label and the extension depends on the methylation state of the respective cytosine in the genomic DNA sample.

It is also preferred according to the invention that the PCR products and/or extension products and/or ligation products are provided with a detectable label for the detection. It is particularly preferred that the labels are fluorescent labels and/or that the labels are radionuclides. It is particularly preferred that the labels of the nucleotides are removable mass labels, which can be detected in a mass spectrometer.

It is also particularly preferred that the PCR products and/or extension products and/or ligation products are detected as a whole in the mass spectrometer and are thus dearly characterized by their mass. It is also preferred according to the invention that a fragment of the PCR products and/or extension products and/or ligation products is detected each time in the mass spectrometer.

The method according to the invention is preferably also characterized by the fact that the fragment of the PCR product and/or extension product and/or ligation product is produced by digestion with one or more exo- or endonucleases.

It is additionally preferred that the produced fragments are provided with an individual positive or negative net charge for better detectability in the mass spectrometer.

It is most particularly preferred that the PCR products and/or extension products and/or ligation products are detected and visualized by means of matrix-assisted laser desorptionrionization mass spectrometry (MALDI-TOF) or by means of electrospray mass spectrometry (ESI).

The method according to the invention is also preferred in which the genomic DNA is obtained from a DNA sample, whereby sources for DNA include, e.g., cell lines, blood, sputum, stool, urine, cerebrospinal fluid, Ussue embedded in paraffin, for example, tissue from eyes, intestine, kidneys, brain, heart, prostate, lungs, breast or liver, histological slide preparations and all possible combinations thereof.

Another subject of the present invention is the use of a method according to the invention for the. diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The subject of the invention is also the use of a method according to the invention for distinguishing cell types or tissues or for investigating cell differentiation.

Another subject of the present invention is finally a kit, comprised of a reagent containing bisulfite, denaturing reagents or solvents, as well as radical traps and primers for the production of amplified products, as well as instructions for conducting an assay according to a method of the invention.

DETAILED DESCRIPTION OF THE INVENTION

The present invention makes available a method for the detection of methylcytosine, which can be automated and which contains only pipetting steps. The efficiency of existing methods is improved in this way relative to simplicity of manipulation, quality, costs, and particularly, throughput.

A method that can be automated for the detection of methylcytosine in genomic DNA samples is described:

The genomic DNA to be analyzed is preferably obtained from the usual sources for DNA, such as, e.g., cell lines, blood, sputum, stool, urine, cerebrospinal fluid, tissue embedded in paraffin, for example, tissue from eyes, intestine, kidneys, brain, heart, prostate, lungs, breast or liver, histological slide preparations and all possible combinations thereof.

In the first step of the method, the DNA utilized is preferably treated with bisulfite (=disulfite, hydrogen sulfite) in such a way that all cytosines not methylated at the 5-position of the base are modified such that a base that differs relative to base pairing behavior is formed, while the cytosines that are methylated in the 5-position remain unchanged.

The genomic DNA sample is thermally denatured most preferably prior to the treatment.

If bisultite in the concentration range between 0.1 and 6 mol/l is used for the reaction, then an addition occurs at the unmethylated cytosine-bases. For the method according to the invention, a denaturing reagent or solvent as well as a radical trap must also be present.

The following compounds or compound classes are considered preferably as denaturing reagents or solvents:

Polyethylene glycol dialkyl ethers, dioxane and substituted derivatives, urea or derivatives, acetonitrile, primary alcohols, secondary alcohols, tertiary alcohols, diethylene glycol dialkyl ethers, triethylene glycol dialkyl ethers, tetraethylene glycol dialkyl ethers, pentaethylene dialkyl ethers, hexaethylene glycol dialkyl ethers, DMSO or THF.

The group of compounds listed in list 1 or their derivatives are preferably suitable as radical traps. The subsequent alkaline hydrolysis then leads to the conversion of unmethylated cytosine nucleobases to uracil.

In the second step of the method, the treated DNA sample is diluted with water or an aqueous solution. Then a desulfonation of the DNA is preferably conducted (10–30 min, 90–100° C.) at alkaline pH.

In the third step of the method, the DNA sample is amplified in a polymerase chain reaction, preferably with a heat-stable DNA polymerase. The amplification of several DNA segments is preferably made in one reaction vessel.

The method step is preferably conducted in two sub-steps. One begins with a PCR preamplification with at least one pair of primers of different sequence, which hybridize non-specifically to the pretreated DNA sample and thus produce more than one amplified product in the PCR step. Then a PCR amplification of the product formed in the preamplification is conducted with primers of different sequence, which are identical each time to one segment of the pretreated DNA sample [(+)-strand or (−)-strand] or vice-versa, are complementary [to it] and specifically hybridize to the DNA to be amplified.

It is thus clear that preamplifications of this type are frequently conducted not as PCR reactions, but as primer extension reactions, which do not require heat-stable polymerase.

In the last step of the method, one detects how much the sequence has been changed due to the treatment with a reagent containing bisulfite in comparison to the genomic DNA sample and the methylation state of at least one locus in the genomic DNA sample is concluded.

The PCR products are most preferably hybridized to an oligonucleotide array for the detection.

In a preferred variant of the method, the following substeps are conducted after the hybridization to an oligonucleotide array:

a) the amplified genomic DNA is hybridized to at least one oligonucleotide with the formation of a duplex, whereby said hybridized oligonucleotides are directly adjacent by their 3' end or at a distance of up to 10 bases to the positions that are to be investigated relative to their methylation in the genomic DNA sample;

(b) the oligonucleotide with known sequence of n nucleotides is extended by at least one nucleotide by means of a polymerase, whereby the nucleotide bears a detectable label and the extension depends on the methylation state of the respective cytosine in the genomic DNA sample.

In another preferred variant of the method, the following substeps are conducted after the hybridizaton to an oligonudeotide array:

(a) a set of oligonucleotides is hybridized to the amplified genomic DNA with the formation of a duplex, whereby this set of oligonucleotides is comprised of two different species and whereby the hybridized oligonucleotides of the first species are directly adjacent by their 3' end or at a distance of up to 10 bases to the positions that are to be investigated relative to their methylation in the genomic DNA sample, and whereby the second oligonucleotide of the second species hybridizes to a second region of the target molecule, so that the 5' end of the oligonucleotide of the second species is separated by a gap of the size of one single nucleotide or up to 10 nucleotides from the 3' end of the hybridized oligonucleotide of the first species at the site of said selected position;

(b) the oligonucleotide of the first species with known sequence of n nucleotides is extended by means of a polymerase by at most the number of nucleotides that lie between the 3' end of the oligonucleotide of the first species and the 5' end of the oligonucleotide of the second species, whereby the extension depends on the methylation state of the respective cytosine in the genomic DNA sample;

(c) the oligonucleotides are incubated in the presence of a ligase, whereby the oligonucleotide of the first species that is extended by the polymerase reaction and the oligonucleotide of the second species are joined and a ligation product is obtained thereby, as long as an extension of the oligonucleoudes of the first species has resulted in the preceding step in such a way that now the 3' end with the present 3' hydroxy function of the extended oligonucleotide is directly adjacent to the 5' end of the oligonucleotide of the second species, which is preferably phosphorylated.

The oligonucleotides of the first species that is used and/or the oligonucleotides of the second species that is used contain in a particularly preferred manner only the bases T, A and C or the bases T, A and G.

In another preferred variant of the method, the following sub-steps are conducted after the hybridization to an oligonucleotide array:

(a) the amplified genomic DNA is hybridized to at least one oligonudeotide with known sequence of n nucleotides with the formation of a duplex, whereby said hybridized oligonucleotides hybridize by their 3' end either partially or completely to the positions that are to be investigated relative to their methylation in the genomic. DNA sample;

(b) as long as it has hybridized by its 3' terminus beforehand without erroneous base pairing to the position to be investigated, the oligonudeotide is extended by at least one nucleotide by means of a polymerase, whereby at least one nucleotide bears a detectable label and the extension depends on the methylation state of the respective cytosine in the genomic DNA sample.

The PCR products and/or extension products and/or ligation products are particularly preferably provided with a detectable label for the detection.

Preferably, the labels of the PCR products and/or extension products and/or ligation products are fluorescent labels, radionuclides or removable mass labels, which are detected in a mass spectrometer.

The PCR products and/or extension products and/or ligation products can preferably be detected as a whole in the mass spectrometer and are thus clearly characterized by their mass.

In a particularly preferred manner, a fragment of the PCR products and/or extension products and/or ligation products is detected each time in the mass spectrometer.

The fragment of the PCR product and/or extension product and/or ligation product is preferably obtained by digestion with one or more exo- or endonucleases.

For better detectability in the mass spectrometer, the obtained fragments most preferably have a single positive or negative net charge.

The PCR products and/or extension products and/or ligation products are detected and visualized preferably by means of matrix assisted laser desorption/ionization mass spectrometry (MALDI-TOF) or by means of electrospray mass spectrometry (ESI).

The present method is preferably used for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The new method also serves in a particularly preferred manner for distinguishing cell types, tissues or for investigating cell differentiation.

The subject of the present invention is also a kit, which contains a reagent containing bisulfite, denaturing reagents or solvents, as well as radical traps according to List 1, primers for the production of the amplified products and instructions for conducting an assay.

List 1:

Di- and trihyroxybenzenes, green tea extract, pine bark extract, gingko biloba extract, (EGb 761), flavonoid mixture of different fruit and vegetable extracts (GMLD), Bio-Normalizer (Sun-O Corp), DPPH (1,1-diphenyl-2-picrylhydrazyl), NDGA (nordihydroguaiaretic acid), Trolox (6-hydroxy-2,5-7,8-tetramethylchromane 2-carboxylic acid), 2,6-di-tert-butylphenol, 4-methyl-di-tert-butylphenol, 4-methoxy-di-tert-butylphenol, 2,6-di-tert-butyl-p-cresol, 3,4-dihydroxybenzoic acid, vitamin C, vitamin E, vitamin Q, hydroquinone, ubiquinone, lignans, hydroxyterpenes, flavonoids, curcumin, tannins, retinoic acid compounds, Ge-132 bis-beta-carboxyethylgermanium sesquioxide, superoxide dismutase (SOD), superoxide catylase, alphanaphthoflavone, di(2-methyl-5-chlorophenyl)dithionate and Cu(II) derivatives, mebendazole, CS (chloroform-soluble) alkyloid extract, 4-(3,5-di-tert-butyl-4-hydroxyphenyl)3-hydroxy-1,2-naphthoquinone, 4-(3,5-di-tert-butyl-4-hydroxyphenyl)3-methoxy-1,2-naphthoquinone, 4-(3,5-di-tert-butyl-4-hydroxyphenyl)1,2-naphthoquinone, 2-(3,5-di-tert-butyl-4-hydroxyphenyl)3-bromo-1,4-naphthoquinone, 2-(3,5-di-tert-butyl-4-hydroxyphenyl)3-chloro-1,4-naphthoquinone, 2-(3,5-di-tert-butyl-4-hydroxyphenyl)3-methoxy-1,4-naphthoquinone, 2-(3,5-di-tert-butyl-4-hydroxyphenyl)3-hydroxy-1,4-naphthoquinone, 2-(3,5-di-tert-butyl-4-hydroxyphenyl)1,4-naphthoquinone, 4-(3,5-di-tert-butyl-4-hydroxyphenyl)3-hydroxy-5,5,8,8-tetramethyl-5,6,7,8-tetrahydro-1,2-anthraquinone, 4-(3,5-di-tert-butyl-4-hydroxyphenyl)3-methoxy-5,5,8,8-tetramethyl-5,6,7,8-tetrahydro-1,2-anthraquinone, 4-(3,5-di-tert-butyl-4-hydroxyphenyl)-5,5,8,8-tetramethyl-5,6,7,8-tetrahydro-1,2-anthraquinone, 3-bromo-4-(3,5-di-tert-butyl-4-hydroxyphenyl)-5,5,8,8-tetramethyl-5,6,7,8-tetrahydro-1,2-anthraquinone, 2-(3,5-di-tert-butyl-4-oxocyclohexa-2,5-dienylidine)indan-1,3-dione, 2-(3,5-di-tert-butyl-4-oxocyclohexa-2,5-dienylidine)3,4-epoxy-3-hydroxymethoxy-(3,4-dihydro-2H-naphthalen-1-one, 2-(3,5-di-tert-butyl-4-oxocyclohexa-2,5-dienylidine)3,4-epoxy-3,4-dimethoxy-(3,4-dihydro-2H-naphthalen-1-one, 2-3,5-di-tert-butyl-4-hydroxyphenyl)indan-1-one, 3,3-bi-[2-(3,5-di-tert-butyl-4-hydroxyphenyl)indan-1-on]-3-yl, 2-(3,5-di-tert-butyl-4-hydroxyphenyl)3-bromo-5,5,8,8-tetramethyl-5,6,7,8-tetrahydro-1,4-anthraquinone, 2-(3,5-di-tert-butyl-4-hydroxyphenyl)3-chloro-5,5,8,8-tetramethyl-5,6,7,8-tetrahydro-1,4-anthraquinone, 2-(3,5-di-tert-butyl-4-hydroxyphenyl)3-methoxy-5,5,8,8-tetramethyl-5,6,7,8-tetrahydro-1,4-anthraquinone, 2-(3,5-di-tert-butyl-4-hydroxyphenyl)3-hydroxy-5,5,8,8-tetramethyl-5,6,7,8-tetrahydro-1,4-anthraquinone, 2-(3,5-di-tert-butyl-4-hydroxyphenyl)-5,5,8,8-tetramethyl-5,6,7,8-tetrahydro-1,4-anthraquinone, 2-bromo-3-(3-bromo-5-tert-butyl-4-hydroxyphenyl)-5,5,8,8-tetramethyl-5,6,7,8-tetrahydro-1,4-anthraquinone, 2-bromo-3-(3,5-dibromohydroxypheny)-5,5,8,8-tetramethyl-5,6,7,8-tetrahydro-1,4-anthraquinone, 2-bromo-3-(3-bromo-5-tert-butyl-4-hydroxyphenyl)3-hydroxy-5,5,8,8-tetramethyl-5,6,7,8-tetrahydro-1,4-anthraquinone, 3-bromo-2-(3,5-di-tert-butyl-4-hydroxyphenyl)1,4-anthroquinone, 2-(3,5-di-tert-butyl-4-hydroxyphenyl)3-methoxy-1,4-anthraquinone, 2-(3,5-di-tert-butyl-4-hydroxyphenyl)3-hydroxy-1,4-anthraquinone, 5,5,8,8-tetramethyl-5,6,7,8-tetrahydronapthalene-1,3-diol, 3-methoxy-5,5,8,8-tetramethyl-5,6,7,8-tetrahydronaphthalen-1-ol, 4-(3-chloro-5,5,8,8-tetramethyl-1,4-dioxo-1,4,5,6,7,8-hexahydroanthracen-2-yl)benzoic acid, methyl-4-(3-chloro-5,5,8,8-tetramethyl-1,4-dioxo-1,4,5,6,7,8-hexahydroanthracen-2-yl)benzoate, 4-(3-hydroxy-1,4-dioxo-1,4-dihydronaphthalen-2-yl)benzoic acid, methyl-(3-methoxy-1,4-dioxo-1,4-dihydronaphthalen-2-yl)benzoic acid, 4-(3-hydroxy-5,5,8,8-tetramethyl-1,4-dioxo-1,4,5,6,7,8-hexahydroanthracen-2-yl)benzoic acid, methyl-4-(3-hydroxy-1,4-dioxo-1,4-dihydronaphthalen-2-yl-azo)benzoate, 4-(3hydroxy-5,5,8,8-tetramethyl-1,4-dioxo-1,4,5,6,7,8-hexahydroanthracen-2-yl-azo)benzoic acid, 3-(3,5-di-tert-butyl-4-oxocyclohexa-2,5-dienylidine)5,5,8,8-tetramethyl-5,6,7,8-tetrahydrocyclopenta[b]naphthalen-1,2-dione, 3-(3,5-di-tert-butyl-4-oxocyclohexa-2,5-dienylidene)5,5,8,8tetramethyl-5,6,7,8-tetrahydroanthracen-3H-1,2,4-trione, 2-(3,5-di-tert-butyl-4-hydroxyphenyl)3-methoxy-5,8-dimethyl-1,4-naphthoquinone, 2-(3,5-di-tert-butyl-4-hydroxyphenyl)3-methoxy-6,7-dimethyl-1,4-naphthoquinone, 2-(3,5-di-tert-butyl-4-hydroxyphenyl)3-methoxy-5-methyl-1,4-naphthoquinone, 2-(3,5-di-tert-butyl-4-hydroxyphenyl)2-methoxy-5-methyl-1,4-naphthoquinone, 2-(3,5-di-tert-butyl-4-hydroxyphenyl)3-methoxy-6-methyl-1,4-naphthoquinone, 3-(3,5-di-tert-butyl-4-hydroxyphenyl)2-methoxy-6-methyl-1,4-naphthoquinione, 2-(3,5-di-tert-butyl-4-hydroxyphenyl)3-methoxy-5,6-dimethyl-1,4-naphthoquinione, 3-(3,5-di-tert-butyl-4-hydroxyphenyl)2-methoxy-5,6-dimethyl-1,4-naphthoquinone, 2-(3,5-di-tert-butyl-hydroxyphenyl)-3-methoxy-5,7-dimethyl-1,4-naphthoquinone, 3-(3,5-di-tert-butyl-4-hydroxyphenyl)2-methoxy-5,7-dimethyl-1,4-naphthoquinone, 2-(3,5-di-tert-butyl-4-hydroxyphenyl)3-ethylthio-5-methyl-1,4-naphthoquinone, 2-(3,5-di-tert-butyl-4-hydroxyphenyl)3-ethylthio-6-methyl-1,4-naphthoquinone, 2-(3,5-di-tert-butyl-4-hydroxyphenyl)3-hydroxy-5,8-dimethyl-1,4-naphthoquinone, 2-(3,5-di-tert-butyl-4-hydroxyphenyl)-3-hydroxy-6,7-dimethyl-1,4-naphthoquinone, 2-(3,5-di-tert-butyl-4-hydroxyphenyl)3-hydroxy-5-methyl-1,4-naphthoquinone, 3-(3,5-di-tert-butyl-4-hydroxyphenyl)2-hydroxy-5-methyl-1,4-naphthoquinone, 2-(3,5-di-tert-butyl-4-hydroxyphenyl)3-hydroxy-6-methyl-1,4-naphthoquinone, 3-(3,5-di-tert-butyl-4-hydroxyphenyl)2-hydroxy-6-methyl-1,4-naphthoquinone, 2-(3,5-di-tert-butyl-4-hydroxyphenyl)3-hydroxy-5,6-dimethyl-1,4-naphthoquinone, 2-(3-bromo-5-tert-butyl-4-hydroxyphenyl)3-hydroxy-5,6-dimethyl-1,4-naphthoquinone, 3-(3,5-di-tert-butyl-4-hydroxyphenyl)-2-hydroxy-5,6-dimethyl-1,4-naphthoquinone, 2-(3,5-di-tert-butyl-4-hydroxyphenyl)3-hydroxy-5,7-dimethyl-1,4-naphthoquinone, 3-(3,5-di-tert-butyl-4-hydroxyphenyl)2-hydroxy-5,7-dimethyl-1,4-naphthoquinone.

The following example explains the invention.

EXAMPLE

Automated Conduction of the Bisulfite Reaction

The application of the method for detecting the methylation state of cytosines in the factor VIII gene of a genomic DNA sample, which was treated with a restriction endonuclease according to the instructions of the manufacturer, is described in the present example. The method is based on the use of an automatic pipetting system (MWG RoboSeq 4204) with four separate vertically movable adapters for exchangeable pipetting tips, so as to exclude cross contaminations. The pipetting system makes possible the pipetting of 100 μl [aliquots] with an error of less than ±2 μl. The operating plate of the automatic pipetting system is equipped with six racks for pipetting tips and eight pipetting positions, two of which can be cooled, a reagent rack that can be cooled, a stacking system for 10 microtiter plates, a pipette tip washing station and a device for separating the pipette tips from the adapter.

The automatic pipetting system is connected to a computer by means of a serial interface and is controlled by means of a software program, which permits. the free programming of all pipetting steps necessary for the application of the method.

In the first step of the method, an aliquot of the DNA sample is pipetted by hand into one of the 96 freely selectable positions of a microtiter plate. The microtiter plate is then subsequently heated to 96 ° C. with the use of an. Eppendorf MasterCycler for denaturing the pretreated DNA sample. The microtiter plate is then transferred to the automatic pipetting system. Aliquots of a denaturing agent (dioxane), a 3.3 M sodium hydrogen sulfite solution, and a solution of a radical trap in the denaturing agent used are pipetted one after the other in a program-controlled manner from the reagent rack into all positions that contain DNA. Then the microtiter plate is incubated in the Eppendorf Mastercycler, so that all unmethylated cytosine residues in the DNA sample are converted into a bisulfite adduct with the action of the sodium hydrogen sulfite.

After the bisulfite treatment, the microtiter plate is transferred from the thermocycler to the automatic pipetting system. A second microtiter plate of the same type is then positioned. First, a basic Tris-HCl buffer (pH 9.5) and then an aliquot of the bisulfite-treated DNA are transferred into the corresponding positions of the second microtiter plate in all chambers whose equivalent positions on the first microtiter plate contain a bisulfite-treated DNA sample. The bisulfite adducts of the unmethylated cytosine residues are converted to uracil residues in the basic solution.

Figure 1:
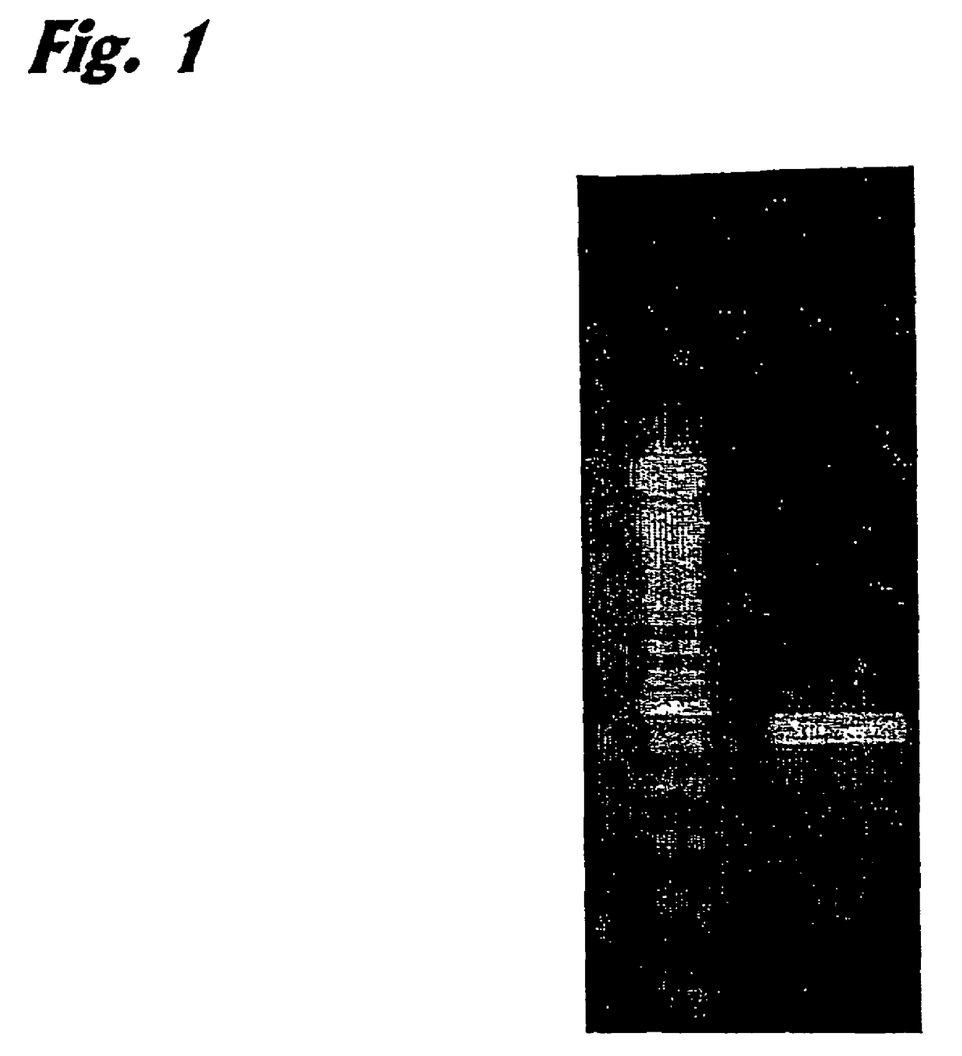
FIG. 1 is a gel image of a PCR-amplified bisulfite-treated DNA strand obtained according to the Example.

The targeted amplification of one strand (the sense strand in the present example) of the bisulfite-treated DNA is conducted by a polymerase chain reaction (PCR). A pair of primers of type 1 (AGG GAG TTT TTT TTA GGG AAT AGA GGG A (SEQ. ID: 1) and TAA TCC CAA AAC CTC TCC ACT ACA ACA A (SEQ ID: 2) are used, which permit the specific amplification of a successfully bisulfite-treated DNA strand, but not a DNA strand, whose unmethylated cytosine residues were not converted to uracil residues or were incompletely converted. A third microtiter plate of the same type is positioned in the automatic pipetting system for the PCR reaction. In all chambers, whose equivalent positions on the first microtiter plate contain a bisulfite-treated DNA sample, an aliquot of a stock solution, which contains a PCR buffer, a DNA polymerase and a primer of type 1 is first automatically pipetted. Then, an aliquot of the diluted-bisulfite-treated DNA is transferred automatically from each position of the second microtiter plate to the corresponding position of the third microtiter plate, before the latter is transferred to the cycler for conducting the PCR reaction. The PCR product is identified by agarose gel electrophoresis and subsequent staining with ethidium bromide (FIG. 1). FIG. 1 shows the gel image of a PCR-amplified bisulfite-treated DNA strand (left: molecular weight marker, right: PCR product).

b) the treated DNA sample is diluted with water or an aqueous solution;
c) the DNA sample is amplified in a polymerase reaction to yield amplified DNA;
d) one detects how much the sequence has changed by the treatment according to step a) in comparison to the genomic DNA sample and concludes the methylation state of at least one locus in the genomic DNA sample.

2. The method according to claim 1, further characterized in that the denaturing solvent is selected from the following list of compounds or compound classes:
Polyethylene glycol dialkyl ethers, dioxane and substituted derivatives, acetonitrile, primary alcohols, secondary alcohols, tertiary alcohols, diethylene glycol dialkyl ethers, triethylene glycol dialkyl ethers, tetraethylene glycol dialkyl ethers, pentaethylene glycol dialkyl ethers, hexaethylene glycol dialkyl ethers, DMSO, THF.

3. The method according to claim 1 or 2, further characterized in that the radical trap is selected from the following group of compounds:
Di- and trihyroxybenzenes, green tea extract, pine bark extract, gingko biloba extract, DPPH (1,1-diphenyl-2-picrylhydrazyl), NDGA (nondihydroguaiaretic acid), 6-hydroxy-2,5-7,8-tetramethylchromine 2-carboxylic acid, 2,6-di-tert-butylphenol, 4-methyl-di-tert-butylphenol, 4-methoxy-di-tert-butylphenol, 2,6-di-tert-butyl-p-cresol, 3,4-dihydroxybenzonic acid, vitamin C, vitamin E, vitamin Q, hydroquinone, ubiquinone, lignans, hydroxyterpenes, flavonoids, curcumin, tannins,

The invention claimed is:

1. A method for the detection of cytosine methylations in DNA is hereby characterized in that the following operating steps are conducted:
a) a genomic DNA sample is incubated with a solution of a bisulfite in the concentration range between 0.1 and 6 mol/liter in the presence of at least one radical trap and at least one denaturing solvent;

retinoic acid compounds, Ge-132bis-beta-carboxyethylgermanium sesquioxide, superoxide dismutase (SOD), superoxide catylase, alpha-naphthoflavone, di(2-methyl-5-chlorophenyl)dithionate and Cu(II) derivatives, mebendazole, CS (chloroform-soluble) alkyloid extract, 4-(3,5-di-tert-butyl-4-hydroxyphenyl) 3-hydroxy-1,2-naphthoquinone, 4-(3,5-di-tert-butyl-4-hydroxyphenyl)-3-methoxy-1,2-naphthoquinone, 4-(3, 5-di-tert-butyl-4-hydroxyphenyl)1,2-naphthoquinone, 2-(3,5-di-tert-butyl-4-hydroxyphenyl) 3-bromo-1,4-naphthoquinone, 2-(3,5-di-tert-butyl-4-hydroxyphenyl) 3-chloro-1,4-naphthoquinone, 2-(3,5-di-tert-butyl-4-hydroxyphenyl) 3-methoxy-1,4-naphthoquinone, 2-(3,5-di-tert-butyl-4-hydroxyphenyl) 3-hydroxy-1,4-naphthoquinone, 2-(3,5-di-tert-butyl-4-hydroxyphenyl)1,4-naphthoquinone, 4-(3,5-di-tert-butyl-4-hydroxyphenyl) 3-hydroxy-5,5,8,8-tetramethyl-5,6,7,8-tetrahydro-1,2-anthraquinone, 4-(3,5-di-tert-butyl-4-hydroxyphenyl)3-methoxy-5,5,8,8-tetramethyl-5,6,7,8-tetrahydro-1,2-anthraquinone, 4-(3,5-di-tert-butyl-4-hydroxyphenyl)-5,5,8,8-tetramethyl-5,6,7,8-tetrahydro-1,2-anthraquinone, 3-bromo-4-(3,5-di-tert-butyl-4-hydroxyphenyl)-5,5,8,8-tetramethyl-5,6,7,8-tetrahydro-1,2-anthraquinone, 2-(3,5-di-tert-butyl-4-oxocyclohexa-2,5-dienylidine)indan-1,3-dione, 2-(3,5-di-tert-butyl-4-oxocyclohexa-2,5-dienylidine) 3,4-epoxy-3-hydroxy-4-methoxy-3,4-dihydro-2H-naphthalen-1-one, 2-(3,5-di-tert-butyl-4-oxocyclohexa-2,5-dianylidine)3,4-epoxy-3,4-dimethoxy-3,4-dihydro-2H-naphthalen-1-one, 2-(3,5-di-tert-butyl-4-hydroxyphenyl)indan-1-one, 3,3-bi-[2-(3,5-di-tert-butyl-4-hydroxyphenyl)indan-1-on]-3-yl, 2-(3,5-di-tert-butyl-4-hydroxypbenyl) 3-bromo-5,5,8,8-tetramethyl-5,6,7,8-tetrahydro-1,4-anthraquinone, 2-(3,5-di-tert-butyl-4-hydroxyphenyl) 3-chloro-5,5,8,8-tetramethyl-5,6,7,8-tetrahydro-1,4-anthraquinone, 2-(3,5-di-tert-butyl-4-hydroxyphenyl)3-methoxy-5,5,8,8-tetramethyl-5,6,7,8-tetrahydro-1,4-anthraquinone, 2-(3,5-di-tert-butyl-4-hydroxyphenyl)3-hydroxy-5,5,8,8-tetramethyl-5,6,7,8-tetrahydro-1,4-anthraquinone, 2-(3,5-di-tert-butyl-4-hydroxyphenyl)-5,5,8,8-tetramethyl-5,6,7,8-tetrahydro-1,4-anthraquinone, 2-bromo-3-(3-bromo-5-tert-butyl-4-hydroxyphenyl)-5,5,8,8-tetramethyl-5,6,7,8-tetrahydro-1,4-anthraquinone, 2-bromo-3-(3,5-dibromo-4-hydroxyphenyl)-5,5,8,8-tetramethyl-5,6,7,8-tetrahydro-1,4-anthraquinone, 2-bromo-3-(3-bromo-5-tert-butyl-4-hydroxyphenyl)3-hydroxy-5,5,8,8-tetramethyl-5,6,7,8-tetrahydro-1,4-anthraquinone, 3-bromo-2-(3,5-di-tert-butyl-4-hydroxyphenyl)1,4-anthroquinone, 2-(3,5-di-tert-butyl-4-hydroxyphenyl)3-methoxy-1,4-anthraquinone, 2-(3,5-di-tert-butyl-4-hydroxyphenyl)3-hydroxy-1,4-anthraquinone, 5,5,8,8-tetramethyl-5,6,7,8-tetrahydronapthalen-1,3-diol, 3-methoxy-5,5,8,8-tetramethyl-5,6,7,8-tetrahydronaphthalen-1-ol, 4-(3-chloro-5,5,8,8-tetramethyl-1,4-dioxo-1,4,5,6,7,8-hexahydroanthracen-2-yl)benzoic acid, methyl-4-(3-chloro-5,5,8,8-tetramethyl-1,4-dioxo-1,4,5,6,7,8-hexahydroanthracen-2-yl)benzoate, 4-(3-hydroxy-1,4-dioxo-1,4-dihydronaphthalen-2-yl)benzoic acid, methyl-(3-methoxy-1,4-dioxo-1,4-dihydronaphthalen-2-yl benzoic acid, 4-(3-hydroxy-5,5,8,8-tetramethyl-1,4-dioxo-1,4,5,6,7,8-hexahydroanthracen-2-yl)benzoic acid, methyl-4-(3-hydroxy-1,4-dioxo-1,4-dihydronaphthalen-2-yl-azo)benzoate, 4-(3-hydroxy-5,5,8,8-tetramethyl-1,4-dioxo-1,4,5,6,7,8-hexahydroanthracen-2-yl-azo)benzoic acid, 3-(3,5-di-tert-butyl-4-oxocyclohexa-2,5-dienylidine)5,5,8,8-tetramethyl-5,6,7,8-tetrahydrocyclopenta[b]naphthalen-1,2-dione, 3-(3,5-di-tert-butyl-4-oxocyclohexa-2,5-dienylidene)5,5,8,8-tetramethyl-5,6,7,8-tetrahydroanthracen-3H-1,2,4-trione, 2-(3,5-di-tert-butyl-4-hydroxyphenyl)3-methoxy-5,8-dimethyl-1,4-naphthoquinone, 2-(3,5-di-tert-butyl-4-hydroxyphenyl)3-methoxy-6,7-dimethyl-1,4-naphthoquinone, 2-(3,5-di-tert-butyl-4-hydroxyphenyl)3-methoxy-5-methyl-1,4-naphthoquinone, 2-(3,5-di-tert-butyl-4-hydroxyphenyl)2-methoxy-5-methyl-1,4-naphthoquinone, 2-(3,5-di-tert-butyl-4-hydroxyphenyl)3-methoxy-6-methyl-1,4-naphthoquinone, 3-(3,5-di-tert-butyl-4-hydroxyphenyl)2-methoxy-6-methyl-1,4-naphthoquinione, 2-(3,5-di-tert-butyl-4-hydroxyphenyl)3-methoxy-5,6-dimethyl-4-naphtoquinione, 3-(3,5-di-tert-butyl-4-hydroxyphenyl)2-methoxy-5,6-dimethyl-1,4-naphthoquinone, 2-(3,5-di-tert-butyl-4-hydroxyphenyl)-3-methoxy-5,7-dimethyl-1,4-naphthoquinone, 3-(3,5-di-tert-butyl-4-hydroxyphenyl)2-methoxy-5,7-dimethyl-1,4-naphthoquinone, 2-(3,5-di-tert-butyl-4-hydroxyphenyl)3-ethylthio-5-methyl-1,4-naphthoquinone, 2-(3,5-di-tert-butyl-4-hydroxyphenyl)3-ethylthio-6-methyl-1,4-naphthoquinone, 2-(3,5-di-tert-butyl-4-hydroxyphenyl)-3-hydroxy-5,8-dimethyl-1,4-naphthoquinone, 2-(3,5-di-tert-butyl-4-hydroxyphenyl)-3-hydroxy-6,7-dimethyl-1,4-naphthoquinone, 2-(3,5-di-tert-butyl-4-hydroxyphenyl)-3-hydroxy-5-methyl-1,4-naphthoquinone, 3-(3,5-di-tert-butyl-4-hydroxyphenyl)-2-hydroxy-5-methyl-1,4-naphthoquinone, 2-(3,5-di-tert-butyl-4-hydroxyphenyl)-3-hydroxy-6-methyl-1,4-naphthoquinone, 3-(3,5-di-tert-butyl-4-hydroxyphenyl)-2-hydroxy-6-methyl-1,4-naphthoquinone, 2-(3,5-di-tert-butyl-4-hydroxyphenyl)3-hydroxy-5,6-dimethyl-1,4-naphthoquinone, 2-(3-bromo-5-tert-butyl-4-hydroxyphenyl)3-hydroxy-5,6-dimethyl-1,4-naphthoquinone, 3-(3,5-di-tert-butyl-4-hydroxyphenyl)-2-hydroxy-5,6-dimethyl-1,4-naphthoquinone, 2-(3,5-di-tert-butyl-4-hydroxyphenyl)3-hydroxy-5,7-dimethyl-1,4-naphthoquinone, 3-(3,5-di-tert-butyl-4-hydroxyphenyl)2-hydroxy-5,7-dimethyl-1,4-naphthoquinone.

4. The method according to claim 1, further characterized in that the genomic DNA sample is thermally denatured prior to the treatment.

5. The method according to claim 1, further characterized in that step c) is conducted in two substeps as follows:
   a) a PCR preamplification with at least one pair of primers of different sequence, which hybridize nonspecifically to a DNA sample pretreated according to claim 1 and thus more than one amplified product is produced in the PCR step;
   b) a PCR amplification of the product formed in the preamplification with primers of different sequence, which are identical or complementary to a segment of the DNA sample [(+)-strand or (−)-strand], which has been pretreated according to claim 1 and which specifically hybridize to the DNA to be amplified.

6. The method according to claim 1, further characterized in that the amplification of several DNA segments is conducted in one reaction vessel.

7. The method according to claim 1, further characterized in that a heat-stable DNA polymerase is used for the polymerase reaction.

8. The method according to claim 1, further characterized in that a desulfonation of the DNA is conducted prior to step c).

9. The method according to claim 1, further characterized in that the amplified DNA is hybridized to an oligonucleotide array for the detection of the pretreated DNA and then the following sub-steps are conducted:
- (a) the amplified genomic DNA is hybridized to at least one oligonucleotide with the formation of a duplex, whereby said hybridized oligonucleotides are directly adjacent by their 3' end or at a distance of up to 10 bases to the positions that are to be investigated relative to their methylation in the genomic DNA sample;
- (b) the oligonucleotide with known sequence of n nucleotides is extended by at least one nucleotide by means of a polymerase, whereby the nucleotide bears a detectable label and the extension depends on the methylation state of the respective cytosine in the genomic DNA sample.

10. The method according to claim 1, further characterized in that the amplified DNA is hybridized to an oligonucleotide array for the detection of the pretreated DNA and then the following sub-steps are conducted:
- (a) a set of oligonucleotides is hybridized to the amplified genomic DNA with the formation of a duplex, whereby this set of oligonucleotides is comprised of two different species and whereby the hybridized oligonucleotides of the first species are directly adjacent by their 3' end or at a distance of up to 10 bases to the positions that are to be investigated relative to their methylatian in the genomic DNA sample, and whereby the second oligonucleotide of the second species hybridizes to a second region of the target molecule, so that the 5' end of the oligonucleotide of the second species is separated by a gap of the size of one single nucleotide or up to 10 nucleotides from the 3' end of the hybridized oligonucleotide of the first species at the site of said selected position;
- (b) the oligonucleotide of the first species with known sequence of n nucleotides is extended by means of a polymerase by at most the number of nucleotides that lie between the 3' end of the oligonucleotide of the first species and the 5' end of the oligonucleotide of the second species, wherein the extension depends on the methylation state of the respective cytosine in the genomic DNA sample;
- (c) the oligonucleotides are incubated in the presence of a ligase, whereby the adjacent oligonucleotide of the first species that has been extended by the polymerase reaction and the oligonucleotide of the second species are joined and in tie way a ligation product is obtained, as long as an elongation of the oligonucleotide of the first species has been produced in the preceding step so that now the 3' end with a present 3' hydroxy function of the extended oligonucleotide is directly adjacent to the 5' end of the oligonucleotide of the second species.

11. The method according to claim 10, further characterized in that the oligonucleotides of the first species that are used and/or the oligonucleotides of the second species that are used contain either only the bases T, A and C or the bases T, A and G.

12. The method according to claim 1, further characterized in that the amplified DNA is hybridized to an oligonucleotide array for the detection of the pretreated DNA and then the following sub-steps are conducted:
- (a) the amplified genomic DNA is hybridized to at least one oligonucleotide with known sequence of n nucleotides with the formation of a duplex, whereby said hybridized oligonucleotides hybridize by the 3' end either partially or completely to the positions that are to be investigated relative to their methylation in the genomic DNA sample;
- (b) as long as the oligonucleotide has hybridized by its 3' terminus beforehand without erroneous base pairing to the position to be investigated, it is extended by at least one nucleotide by means of a polymerase, whereby at least one nucleotide bears a detectable label and the extension depends on the methylation state of the respective cytosine in the genomic DNA sample.

13. The method according to claim 1, further characterized in that the amplified DNA is provided with at least one detectable label for detection.

14. The method according to claim 13, further characterized in that the at least one detectable label comprises fluorescent labels.

15. The method according to claim 13, further characterized in that the at least one detectable label comprises radionuclides.

16. The method according to claim 13, further characterized in that the at least one detectable label comprises removable mass labels, which can be detected in a mass spectrometer.

17. The method according to claim 1, further characterized in that the amplified DNA is detected as a whole in the mass spectrometer and thus are characterized by their mass.

18. The method according to claim 1, further characterized in that a fragment of the amplified DNA is detected each time in the mass spectrometer.

19. The method according to claim 18, further characterized in that the fragment of the amplified DNA is produced by digestion with one or more exo- or endonucleases.

20. The method according to claim 18 or claim 19, further characterized in that the produced fragments are provided with a single positive or negative net charge.

21. The method according to claim 1, further characterized in that the amplified DNA is detected and visualized by means of matrix assisted laser desorption/ionization mass spectrometry (MALDI-TOF) or by means of electrospray mass spectrometry (ESI).

22. The method according to claim 1, whereby the genomic DNA is obtained from a DNA sample, whereby sources for DNA comprise cell lines, blood, sputum, stool, urine, cerebrospinal fluid, tissue embedded in paraffin, tissue of eyes, intestine, kidneys, brain, heart, prostate, lungs, breast or liver, histological slide preparations and all possible combinations thereof.

23. Use of a method according to claim 1 for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

24. Use of a method according to claim 1 for distinguishing cell types or tissues or for investigating cell differentiation.

* * * * *

SEQUENCE LISTING

<160> NUMBER OF SEQ ID NOS: 2

<210> SEQ ID NO 1
<211> LENGTH: 28
<212> TYPE: DNA
<213> ORGANISM: Artificial sequence
<220> FEATURE:
<223> OTHER INFORMATION: Description of artificial sequence: Primer

<400> SEQUENCE: 1
agggagtttt ttttagggaa tagaggga                28

<210> SEQ ID NO 2
<211> LENGTH: 28
<212> TYPE: DNA
<213> ORGANISM: Artificial sequence
<220> FEATURE:
<223> OTHER INFORMATION: Description of artificial sequence: Primer

<400> SEQUENCE: 2
taatcccaaa acctctccac tacaacaa                28